United States Patent [19]

Quast

[11] Patent Number: 5,736,158
[45] Date of Patent: Apr. 7, 1998

[54] PARTIAL DENTURE CLEANSER WITH FLUORIDE

[75] Inventor: Marco Quast, Krefeld, Germany

[73] Assignee: The Block Drug Company, Jersey City, N.J.

[21] Appl. No.: 622,769

[22] Filed: Mar. 27, 1996

[51] Int. Cl.$^6$ ........................ A61K 7/30
[52] U.S. Cl. .............. 424/464; 424/466; 424/472; 424/52; 424/55; 424/56; 424/57; 424/53
[58] Field of Search .......................... 424/464, 466, 424/472, 52, 55, 56, 57, 49, 53

[56] References Cited

U.S. PATENT DOCUMENTS

| | | | |
|---|---|---|---|
| 3,962,107 | 6/1976 | Levin | 252/100 |
| 4,256,599 | 3/1981 | Krisp et al. | 252/99 |
| 4,603,045 | 7/1986 | Smigel | 424/52 |
| 4,732,617 | 3/1988 | Causton et al. | 106/35 |
| 4,770,634 | 9/1988 | Pellico | 433/217.1 |
| 4,772,325 | 9/1988 | Kwan et al. | 106/35 |
| 5,055,305 | 10/1991 | Young | 424/466 |
| 5,249,962 | 10/1993 | Ascher | 433/131 |
| 5,304,586 | 4/1994 | Mammesfahr et al. | 523/117 |
| 5,403,579 | 4/1995 | Michaels | 424/54 |
| 5,459,898 | 10/1995 | Bacolot | 15/106 |

*Primary Examiner*—Raj Bawa
*Attorney, Agent, or Firm*—Craig M. Bell; Dann, Dorfman, Herrell and Skillman

[57] ABSTRACT

A composition for the cleaning and protection of partial dentures and the associated natural teeth of the wearer consisting essentially of a peroxy bleach cleanser in an amount of from about 5.0 wt % to about 70.0 wt % of the total weight of the composition; a fluoride source incorporated in a polymer matrix in a polymer/fluoride weight ratio of from about 3:1 to 1:3; at least one surfactant in an amount of from about 3.0 wt % to about 18.0 wt %; an organic peroxy acid bleach in an amount of from about 10.0 wt % to about 40.0 wt %; an active bicarbonate-based effervescent agent in an amount of from about 5.0 wt % to about 65.0 wt %. The composition is formulated as a two-layer compressed tablet wherein one layer contains the peroxyacid bleach cleanser and surfactant while the other layer contains the fluoride and a surfactant. The partial dentures are oxidized by the peroxy bleach and they retain at least a portion of fluoride on the surface of the denture for the sustained delivery to the natural teeth once the partial denture is placed back into the mouth.

16 Claims, No Drawings

PARTIAL DENTURE CLEANSER WITH FLUORIDE

FIELD OF THE INVENTION

The present invention relates generally to oral care and dental hygiene. More particularly, the invention relates to cleaning compositions for both oral prostheses such as partial dentures and naturally retained human teeth.

BACKGROUND OF THE INVENTION

Numerous formulations have been available over the years for the cleaning and care of full dentures and other dental prostheses which merely involve removal of the article from the mouth and placing it in a solution or manually brushing it with a dental cream or paste. Recently however, better oral hygiene and care has resulted in the increasing use of partial dentures which are inserted and substituted for several teeth rather than the entire mandibular arch. This will be placed in spaces where one or more teeth are missing and there is no root present for the attachment of a dental cap or bridge. The partial denture generally fills these spaces and is secured to the jaw by attachment to the adjacent natural teeth. A patient with partial dentures however, not only has the problem of cleaning the partial dentures but also must clean and care for the remaining natural teeth.

A particular problem that arises for partial denture wearers are those areas of the natural teeth which abut against or are in contact with the partial denture. At these points where the dentures and normal teeth are in contact, the natural teeth are subjected to unusual stress and exposure. Food particles often tend to clog in these sections which become harder to clean and this leads to a higher incidence of tartar deposit and decay. Whereas many cleanser formulations exist which will clean the partial denture thoroughly, nothing is available which will clean and protect both the partial denture and afford continuous protection to the surrounding natural teeth.

U.S. Pat. No. 4,256,599 to Krisp et al. disclose and claim a two-layered denture cleansing tablet in which sulfonic acid is contained in a first layer which disintegrates and serves as a first cleaning step. Ethylene diaminetetraacetic acid (EDTA) is contained in both layers and provides a softening and demineralization function and allegedly dissolves tartar and plaque deposits as well. The cleaning agents are delivered in an effervescent tablet which, through the release of carbon dioxide bubbles, are agitated about the dentures in what is tantamount to a "scrubbing" action.

U.S. Pat. No. 4,603,045 to Smigel discloses a toothpaste composition that exhibits cleaning efficacy and tooth decay protection for both natural teeth and the composite resin filling material used to fill cavities and other lesions of the tooth. The composition utilizes a number of carbonates and peroxides with a surfactant to provide the asserted cleaning efficacy.

U.S. Pat. No. 4,732,617 to Causton et al. discloses prophylactic and therapeutic fluoride compositions which are comprised of a fluoride source that is incorporated into a poly(organophosphate) polymer. This is permeable to fluoride ions and releases them slowly over time. The material may be administered as a paste, foam or mouthwash and is asserted to provide long-lasting fluoride protection as the fluoride/polymer blend adheres to the teeth and gums.

U.S. Pat. No. 4,772,325 to Kwan et al. also discloses a fluoride-containing dental composition which is used as a composite filling for cavities, as an orthodontic resin, or as a pit and fissure sealant. The fluoride source, such as boron trifluoride, is contained in a Lewis base/Lewis acid combination which slowly releases the fluoride to prevent further development of dental caries and to reduce plaque formation. The composition may also be used in conjunction with other dental resins, cements, sealants and restorative materials.

U.S. Pat. No. 5,055,305 to Young discloses and claims a denture cleaning tablet comprised of an inorganic persalt bleaching agent, an organic peroxyacid bleach precursor and an acid/carbonate base material which provides the effervescence. The tablet is formulated so that the alkaline phase dissolves slower than the acid which allegedly provides greater cleaning efficacy.

Finally, U.S. Pat. No. 5,304,586 to Hammesfahr et al. discloses dental composites comprised of ground glass filler material that are used as tooth restorative compositions. These also contain a fluoride ion source that slowly leaches therefrom and serves to protect against dental caries. The restorative material is light cured in-situ and retains its shape and strength even after the fluoride is substantially depleted therefrom.

Whereas most or all of the prior art compositions can be used to clean and protect the partial denture or ones natural teeth, none of them provide a composition that delivers cleaning efficacy and fluoride protection for both. Different compositions must be used in different applications or steps and again the problems discussed earlier are not resolved. There is a need then, for a dental cleanser that by itself will clean both the partial denture, and provide fluoride protection to the surrounding natural teeth.

SUMMARY OF THE INVENTION

The present invention comprises a dental cleanser for the cleaning of partial dentures with the added benefit of providing fluoride protection to the wearers natural teeth when the partial denture is subsequently placed back into the mouth. Preferably the cleanser will be provided in a two-layer tablet with a peroxy bleach cleanser contained in one layer and the sustained release fluoride source in the other. The composition may also be applied as a paste, cream, mouthwash or gel.

DETAILED DESCRIPTION OF THE INVENTION

The dental cleanser of the present invention is essentially a combination of two active ingredients which perform two distinctly different, albeit important functions. As a result, the cleanser composition is preferably formulated as two layer tablet in which a peroxyacid bleach cleanser and a surfactant are kept in one layer while fluoride and the surfactant are incorporated in the other. Both layers exhibit different rates of dissolution and release. The peroxyacid bleach cleans and brightens the partial denture while the fluoride component, self-contained in a polymer adhesive, adheres to the denture and is released to coat the surrounding teeth when the denture is placed back into the oral cavity.

Preferably, the partial denture fluoride cleanser is formulated as a two layer effervescent tablet which, when placed in water, generates active oxygen bubbles which agitate the cleanser water and aid in the physical scrubbing of the porcelain surface of the denture. The two layers are comprised of an acid portion and an alkali or carbonate portion which react upon dissolution and release the oxygen into the surrounding water.

The actual cleanser for the partial dentures is an active oxygen compound or bleach known in the art which cleans the porcelain surface of the denture though oxidizing action. The oxidizing agent may take the form of an inorganic persalt and can be selected from any of the well-known bleaching agents known for use in denture cleansers such as the alkali metal and ammonium persulfates, perborates and perphosphates as well as the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. More specifically these include sodium perborate monohydrate, potassium persulfate, sodium carbonate peroxide, diperisophthalic acid, potassium peroxydiphosphate and mixtures thereof. Of these, however, the alkali metal persulfates, perborates and mixtures thereof are highly preferred for use herein.

The amount of bleaching agent in the total composition is generally from about 5.0% to about 70% by weight of the total weight of the tablet and preferably from about 10% to about 50% by weight. In the preferred compositions comprising the mixture of alkali metal persulfates and perborates, the overall persulfate:perborate ratio is preferably from about 5:1 to about 1:5 and more preferably from about 2:1 to about 1:2, respectively.

A fluoride source is also provided for the prevention of dental caries in the associated natural teeth within which the partial denture is maintained. Fluoride ions themselves provide both a systemic and a topical benefit to teeth. Along with helping to prevent cavities, fluoride enhances the resistance of dental enamel to acid attack. By providing the fluoride source in a polymer adhesive vehicle, the fluoride is introduced to the mouth by way of the cleaned partial denture which, when cleaned with the composition of the present invention, has the fluoride/adhesive polymer composition coated thereon. Upon contact with the saliva of the oral cavity, the fluoride ions are slowly released from the polymer adhesive and serve to protect the surrounding natural teeth.

Any one of a number of fluoride compositions may be incorporated in the dental cleanser of the present invention as a source of fluoride ion. Stannous fluoride and sodium fluoride are perhaps the best known and most widely utilized sources of fluoride in the art but other forms include, without limitation, calcium fluoride, potassium fluoride, lithium fluoride, aluminum fluoride, ammonium fluoride, zinc fluoride, zirconium fluoride, sodium monofluorophosphate, acidulated phosphate fluoride, aminofluoride, stannous chlorofluoride, magnesium fluoride, potassium trifluorostannous, stannous hexafluorozirconate, titanium fluoride, iron fluoride and mixtures thereof. Stannous fluoride is most preferred however.

The source of fluoride is combined with a natural or synthetic polymer adhesive so as to be able to attach to the partial denture for protection of the natural teeth and gums when released in the mouth. The fluoride/polymer adhesive composition should be formulated so that the fluoride is incorporated on and within the adhesive for the slow sustained release of fluoride ions to the enamel surface of the surrounding natural teeth over time. Suitable polymers include hydrocolloids, cellulose and its derivatives, polyvinyl pyrrolidone, polyvinyl chloride, acrylic and methacrylic esters, vinyl acrylic polymers, polystyrene, polyethylene resins epoxy resins, polypropylene resins, polycarbonates, vinyl styrenes and copolymers comprising mixtures of two or more of these species. Gums such as xanthan gum, guar gum, chicle and the like may also be used.

Preferably however, the fluoride source is incorporated in a lower alkyl vinyl ether maleic acid or anhydride (AVE/MA). Commercially available as Gantrez® (ISP Inc., Wilmington, Del.), this copolymer is obtained by copolymerizing a lower alkyl vinyl ether monomer with maleic acid or maleic anhydride moiety. These polymers may also be cross-linked with an alkali metal salt such as calcium, sodium, zinc, magnesium and the like.

The fluoride ion source and the adhesive may be combined in varying ratios and amounts that are ultimately dictated by the type of delivery system employed; i.e., effervescent tablet, gel, foam, paste, etc. It is most desirable to load as much fluoride into the system as possible and generally the polymer/fluoride ion ratio as a function of weight percentages will range from about 1:3 to about 3:1 respectively. Preferably, the adhesive polymer/fluoride ion ratio will vary from about 1:3 to 1:1. The total amount of the fluoride/polymer adhesive composition will comprise from about 10 weight percent to about 30 weight percent of the total weight of the tablet formulation and preferably about 20 weight percent of the total weight of the tablet composition.

When the denture cleanser/fluoride supplement composition of the present invention is formulated as an effervescent two layer tablet, the bulk majority of the system is the effervescent component. The effervescent solid base material of the compositions herein preferably comprises a combination of at least one alkali metal carbonate or bi-carbonate, such as sodium bicarbonate, sodium carbonate, calcium carbonate, calcium bicarbonate, sodium sesquicarbonate, potassium carbonate, potassium bicarbonate, sodium calcium or potassium hydroxide and mixtures thereof, in admixture with at least one nontoxic, physiologically-acceptable organic acid, such as tartaric, fumaric, citric, malic, maleic, gluconic, succinic, salicylic, adipic or sulfamic acid, sodium fumarate, sodium or potassium acid phosphates, betaine hydrochloride or mixtures thereof. These acid/base combinations produce a vigorous effervescence when in contact with water. The bicarbonate components generally comprise from about 5.0 wt. % to about 65 wt. % and preferably from about 35% to 55% of the total weight of the tablet; the acid components generally comprise from about 5.0 wt. % to about 50 wt. % and preferably from about 20% to about 40% of the total tablet weight.

In preferred embodiments, the solid base material comprises two or more component phases having a differing pH in aqueous medium, at least one of the component phases having an acidic pH. In such compositions, the inorganic bleaching agent preferably comprises an alkali metal and ammonium persulfate, perborate or perphosphate as well as the alkali metal and alkaline earth metal peroxides. These include the potassium, sodium and ammonium perborates, magnesium, calcium and zinc peroxides and the like. The acidic phase incorporates the organic peroxyacid bleach precursor and this comprises preferably from about 10% to about 40% of the total weight of the tablet and preferably from about 15% to about 30% of the alkali metal persulfate.

A surfactant or surface active agent is also incorporated into the denture cleanser/fluoride supplement composition as a detergent for lowering the interfacial surface tension of the denture porcelain surface for maximum fluoride loading during the cleansing step. Suitable surface active agents useful in this capacity are numerous and basically may be any of the ones that are compatible with the other ingredients of the cleanser system. These surfactants will also aid in the removal of any food debris that might be attached to the denture surface.

Surfactants useful to this end are generally anionic and/or non-ionic surfactants. More specifically, suitable surfactants may be selected from the group comprising sodium lauryl sulfate, sodium N-lauryl sarcosinate, sodium lauryl sulfoacetate, dioctyl sodium sulfosuccinate, ricinoleyl sodium sulfosuccinate, sodium tridecyl sulfate, sodium cetyl sulfate, sodium dodecyl benzene sulfonates, sodium myristal sulfate, magnesium lauryl sulfate, potassium lauryl sulfate and mixtures thereof. The amount of surfactant incorporated in the denture cleanser tablet will range from about 3.0 wt. % to about 18.0 wt. % of the total weight of the cleanser composition. Preferably, the surfactant will be incorporated in amounts of from about 7.0 wt. % to about 10.0 wt. % of the entire composition.

The components of the present invention are compressed into a two layer tablet using standard die and tabletting procedures known in the art. The components of each layer are formulated separately, thoroughly mixed and then each is poured into separate but contiguous die which are then compressed and compacted together in a two-layer tabletting machine.

Other excipients such as flavors, sweeteners, tabletting aids, preservatives, binding agents, viscosity modifiers, thickeners, fillers, etc. may be added to the compositions of the present invention as is known in the art and the specific types selected will depend upon what delivery formulation or system is utilized, i.e., effervescent tablet, foam, gel, paste or film. These can be altered or modified according to taste or application and either way a highly effective cleanser/fluoride supplement can be realized.

A chelating or sequestering agent may also be added to the composition particularly in those formulations utilizing peroxygen bleaching agents. Suitable chelators include ethylenediamine tetraacetic acid (EDTA), tetrasodium ethylenediaminetetracetate dihydrate, and diammonium ethylenediaminetriacetate and the like. These may be added to the formulation to sequester the heavy metal ions present in the solution during the tablets dissolution and to prevent the break-down of the bleaching agent.

The following examples are provided to more fully set forth and detail the formulations of the present invention. They are for illustrative purposes only and it is recognized that there are minor changes or alternative embodiments not contemplated therein. It is to be understood however, that to the extent any such change or modification does not materially alter the final product or outcome, such embodiments are to be considered as falling within the spirit and scope of the present invention as recited by the claims that follow.

EXAMPLE I

A two layer effervescent tablet was prepared according to the formulation of the present invention by preparing two separate layer compositions using the following ingredients in their respective weight percents based on the total weight of the tablet compositions.

| Layer 1 | | |
|---|---|---|
| a. | Sodium fluoride | 12.0 wt. % |
| b. | Gantrez ® AVE/MA | 15.0 wt. % |
| c. | Sodium lauryl sulfate | 5.5 wt. % |
| d. | Polyethylene glycol | 1.0 wt. % |
| e. | Magnesium stearate | 1.0 wt. % |

| -continued | | |
|---|---|---|
| Layer 2 | | |
| a. | Sodium bicarbonate | 30.0 wt. % |
| b. | Citric acid | 20.0 wt. % |
| c. | Sodium persulfate | 10.0 wt. % |
| d. | Polyvinyl pyrrolidone | 2.5 wt. % |
| e. | Mint flavor | 1.0 wt. % |
| f. | talc | 2.0 wt. % |

The ingredients are dry mixed as separate batches and are fed into separate hoppers of a two layered tabletting machine. Once the ingredients were fed into the separate die cavities of the press, the layers were compacted into two-layer tablets weighing 3.0 grams each.

Once placed in water, the tablets exhibited a high degree of effervescence which, after a 15–20 minute soak, reduced any visible stains and associated food debris from a number of partial dentures soaked therein.

EXAMPLE II

A fluoride foam for the manual cleaning of partial dentures was prepared using the following ingredients in their respective weight percentages based on the total weight of the foam composition.

| a. | Stannous fluoride | 5.5 wt. % |
|---|---|---|
| b. | Gantrez ® (AVE/MA) | 7.5 wt. % |
| c. | Sodium lauryl sulfate | 3.4 wt. % |
| d. | Glycerol | 4.0 wt. % |
| e. | Citric acid | 8.0 wt. % |
| f. | Wintergreen flavor oil | 2.2 wt. % |
| g. | Phosphoric acid | 1.5 wt. % |
| h. | Sucrose distearate | 2.0 wt. % |
| i. | Water | 63.9 wt. % |

The oral dentifrice was formulated as a gel and a foam depending on whether it was incorporated and packaged directly within a tube or whether it was oxygenated and pressurized in an aerosol container. Either way, the composition was applied to a toothbrush which, when rubbed across the surfaces of several stained partial dentures, removed any visible stains and film. When the dental foam was rinsed from the partial dentures a slippery lubricous film remained on the surface indicating the presence of the AVE/MA polymer encapsulated fluoride.

What is claimed is:

1. A composition for the cleaning and protection of partial dentures and the associated natural teeth of the wearer consisting essentially of:
    a. a peroxy bleach cleanser in an amount of from about 5.0 wt % to about 70.0 wt % of the total weight of the composition;
    b. a fluoride source incorporated in a polymer matrix in a polymer/fluoride weight ratio of from about 3:1 to 1:3;
    c. at least one surfactant in an amount of from about 3.0 wt % to about 18.0 wt %;
    d. an organic peroxyacid bleach in an amount of from about 10.0 wt % to about 40.0 wt %;
    e. an active bicarbonate-based effervescent agent in an amount of from about 5.0 wt % to about 65.0 wt %;
    f. said composition is formulated as a two-layer compressed tablet wherein one layer contains the peroxyacid bleach cleanser and surfactant while the other layer contains said fluoride and a surfactant; wherein said partial dentures are oxidized by said bleach and retain at least a portion of said fluoride on the surface of the denture for the sustained delivery to the natural teeth once the partial denture is placed back into the mouth.

2. The composition of claim 1 wherein said peroxy bleach cleanser is selected from the group consisting of sodium carbonate peroxide, sodium perborate monohydrate, potassium persulfate, sodium persulfate, diperisophthalic acid, sodium pyrophosphate peroxyhydrate, calcium peroxide, potassium peroxydiphosphate, ammonium persulfate and mixtures thereof.

3. The cleanser composition of claim 2 wherein said fluoride source is selected from the group consisting of sodium fluoride, stannous fluoride, zirconium fluoride, potassium fluoride, lithium fluoride, sodium monofluorophosphate, acidulated phosphate fluoride, amino fluoride, stannous chlorofluoride, magnesium fluoride, potassium trifluorostannous, stannous hexafluorozirconate, titanium fluoride, ammonium fluoride, calcium fluoride and mixtures thereof.

4. The cleanser composition of claim 3 wherein said adhesive is selected from the group consisting of hydrocolloids, cellulose, polypropylene resins, polycarbonates, polyethylene resins, polyurethane resins, stannous, polyvinyl pyrrolidone, polyvinyl chloride, acrylic and methacrylic esters, vinyl acrylic polymers, polystyrene, vinyl styrenes and mixtures thereof.

5. The cleanser composition of claim 4 wherein said adhesive is selected from the group consisting of a copolymer of a lower alkyl vinyl ether maleic acid, a lower alkyl vinyl ether maleic anhydride and mixtures thereof.

6. The cleanser composition of claim 5 wherein said surfactant is selected from the group consisting of anionic and nonionic surfactants.

7. The cleanser composition of claim 6 wherein said surfactant is selected from the group consisting of sodium lauryl sulfate, sodium tridecyl sulfate, sodium lauryl sulfoacetate, sodium cetyl sulfate sodium dodecyl benzene sulfonate, sodium myristal sulfate, magnesium lauryl sulfate, potassium lauryl sulfate, N-lauryl sarcosinate, ricinoleyl sodium sulfosuccinate and mixtures thereof.

8. The cleanser composition of claim 7 wherein said effervescent agent is selected from the group consisting of an acid, an alkaline earth metal carbonate or hydroxide and a binder.

9. The cleanser composition of claim 8 wherein said acid is selected from the group consisting of citric acid, tartaric acid, fumaric acid, maleic acid, malic acid, succinic acid, salicylic acid, adipic acid, sulfamic acid, gluconic acid, sodium fumarate, sodium or potassium acid phosphate, betaine hydrochloride and mixtures thereof.

10. The cleanser composition of claim 9 wherein said alkaline earth metal carbonate is selected from the group consisting of sodium carbonate, sodium bicarbonate, calcium carbonate, calcium bicarbonate, potassium carbonate, potassium bicarbonate, sodium hydroxide, calcium hydroxide, potassium hydroxide, sodium sesquicarbonate and mixtures thereof.

11. The cleanser composition of claim 10 wherein said peroxy bleach comprises from about 10 wt. % to about 30 wt. %, based upon the total weight of the cleanser composition.

12. The cleanser composition of claim 11 wherein said fluoride source comprises from about 0.02 wt. % to about 10.0 wt. %, based upon the total weight of the cleanser composition.

13. The cleanser composition of claim 12 wherein said polymer adhesive comprises from about 10.0 wt. % to about 50.0 wt. % of the total weight of the composition.

14. The cleanser composition of claim 13 further comprising a chelating agent.

15. The cleanser of composition of claim 14 wherein said chelating agent is selected from the group consisting of ethylene diaminetetraacetic acid, tetrasodium ethylene diaminetetraacetic acid, tetrasodium ethylene diaminetetraacetate and mixtures thereof.

16. The cleanser composition of claim 15 further comprising flavors, sweeteners, tabletting aids, preservatives, binding agents, viscosity modifiers, fillers, and mixtures thereof.

* * * * *